US012016621B2

United States Patent
Krans et al.

(10) Patent No.: US 12,016,621 B2
(45) Date of Patent: Jun. 25, 2024

(54) FORCE SENSING CATHETER SEALED ELECTRODE TIP ASSEMBLY AND METHODS OF ASSEMBLING SAME

(71) Applicant: ST. JUDE MEDICAL, CARDIOLOGY DIVISION, INC., St. Paul, MN (US)

(72) Inventors: Mark B. Krans, Hopkins, MN (US); James Holmberg, Champlin, MN (US); John J. Buysman, Minnetonka, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 570 days.

(21) Appl. No.: 16/948,014

(22) Filed: Aug. 27, 2020

(65) Prior Publication Data

US 2021/0059747 A1    Mar. 4, 2021

Related U.S. Application Data

(60) Provisional application No. 62/893,439, filed on Aug. 29, 2019.

(51) Int. Cl.
*A61B 18/14*    (2006.01)
*A61B 18/00*    (2006.01)
(Continued)

(52) U.S. Cl.
CPC ...... *A61B 18/1492* (2013.01); *A61B 18/1206* (2013.01); *A61B 90/06* (2016.02);
(Continued)

(58) Field of Classification Search
CPC . A61B 18/1492; A61B 18/1206; A61B 90/06; A61B 2018/00577;
(Continued)

(56) References Cited

U.S. PATENT DOCUMENTS 5,919,188 A * 7/1999 Shearon .................. A61N 1/06
606/41
7,776,034 B2 * 8/2010 Kampa .............. A61B 18/1492
606/41
(Continued)

FOREIGN PATENT DOCUMENTS

| CN | 101416874 A | 4/2009 |
|----|-------------|--------|
| CN | 105581840 A | 5/2016 |
| JP | 2015523106 A | 8/2015 |

OTHER PUBLICATIONS

International Search Report and Written Opinion for International Patent Application No. PCT/US2020/048219, dated Nov. 17, 2020, 11 pages.

*Primary Examiner* — Joseph A Stoklosa
*Assistant Examiner* — Annie L Shoulders
(74) *Attorney, Agent, or Firm* — Armstrong Teasdale LLP

(57) ABSTRACT

Disclosed herein is an ablation catheter that includes an irrigation conduit, a force sensor, an electrode tip assembly, a seal, and a temperature sensor. The irrigation conduit defines an irrigation lumen configured to carry irrigation fluid to a distal end of the ablation catheter. The force sensors include a deformable body coupled to the irrigation conduit adjacent a distal end thereof. The electrode tip assembly is coupled to the deformable body and extends distally therefrom, and defines an interior cavity in fluid communication with the irrigation lumen and an exterior cavity in which a distal portion of the deformable body is received. The seal is disposed between the electrode tip assembly and the deformable body, and inhibits fluid flow between the interior cavity and the exterior cavity. The temperature sensor is coupled to the electrode tip assembly and extends from the electrode tip assembly through the irrigation lumen.

20 Claims, 6 Drawing Sheets

(51) Int. Cl.
*A61B 18/12* (2006.01)
*A61B 90/00* (2016.01)

(52) U.S. Cl.
CPC .............. *A61B 2018/00577* (2013.01); *A61B 2018/00821* (2013.01); *A61B 2090/064* (2016.02); *A61B 2218/002* (2013.01)

(58) Field of Classification Search
CPC .... A61B 2018/00821; A61B 2090/064; A61B 2218/002; A61B 2018/00791
See application file for complete search history.

(56) References Cited

U.S. PATENT DOCUMENTS

| | | | |
|---|---|---|---|
| 8,273,082 B2 * | 9/2012 | Wang ................. | A61B 18/1492 606/41 |
| 8,435,232 B2 | 5/2013 | Aeby et al. | |
| 8,979,837 B2 | 3/2015 | de la Rama et al. | |
| 9,510,903 B2 | 12/2016 | Pappone et al. | |
| 9,597,036 B2 | 3/2017 | Aeby et al. | |
| 10,130,418 B2 | 11/2018 | Wang et al. | |
| 10,363,090 B2 * | 7/2019 | Beeckler ................. | A61B 5/061 |
| 11,026,745 B2 * | 6/2021 | Guler ................. | A61B 18/1492 |
| 2009/0163911 A1 * | 6/2009 | Cao ..................... | A61B 18/1492 606/41 |
| 2009/0287092 A1 * | 11/2009 | Leo ......................... | A61B 90/06 385/12 |
| 2014/0276788 A1 * | 9/2014 | Nguyen ............. | A61B 18/1492 606/41 |
| 2014/0364848 A1 | 12/2014 | Heimbecher et al. | |
| 2015/0351832 A1 * | 12/2015 | Oliverius ............. | A61B 5/6852 606/41 |
| 2015/0374252 A1 * | 12/2015 | delLa Rama ........ | A61B 5/6869 606/41 |
| 2017/0143417 A1 * | 5/2017 | Wang ................. | A61B 18/1492 |
| 2018/0085158 A1 * | 3/2018 | Aeby ................. | A61B 18/1492 |
| 2018/0199976 A1 * | 7/2018 | Fischer ................. | A61B 18/02 |
| 2018/0353238 A1 * | 12/2018 | Schultz ............... | A61B 18/1492 |
| 2019/0036228 A1 | 2/2019 | Daly et al. | |
| 2019/0083173 A1 | 3/2019 | Wang et al. | |

\* cited by examiner

FORCE SENSING CATHETER SEALED ELECTRODE TIP ASSEMBLY AND METHODS OF ASSEMBLING SAME

This application claims priority to U.S. provisional patent application Ser. No. 62/893,439, filed Aug. 29, 2019, the disclosure of which is hereby incorporated by reference in its entirety.

BACKGROUND OF THE DISCLOSURE a. Field of the Disclosure

The present disclosure relates generally to electrophysiological (EP) catheters. More particularly, the present disclosure relates to ablation systems including an EP catheter including a force sensor and a sealed electrode tip assembly that prevents irrigation fluid from interfering with the force sensor.

b. Background

Electrophysiology catheters are used for an ever-growing number of medical procedures. For example, catheters are used for diagnostic, therapeutic, and ablative procedures. Typically, the catheter is manipulated through a patient's vasculature and to the intended site, such as a site within the patient's cardiovascular system, such as the heart or renal artery.

A catheter may carry one or more electrodes, which may be used for ablation, mapping, diagnosis, or the like. Tissue ablation may be used to treat a variety of clinical disorders. For example, tissue ablation may be used to treat cardiac arrhythmias by destroying aberrant pathways that would otherwise conduct abnormal electrical signals to the heart muscle. Several ablation techniques have been developed, including cryoablation, microwave ablation, radio frequency (RF) ablation, and high frequency ultrasound ablation.

Because RF ablation may generate significant heat, it may be desirable to monitor the temperature of the ablation assembly during an ablation procedure. The temperature of the ablation assembly may be monitored during a procedure using a thermocouple, which may sometimes be placed within the tip of one or more electrodes of the ablation assembly. Such thermocouples are conventionally routed from an exterior of the ablation assembly to an interior thereof, and to an electrode tip for temperature measurement adjacent the ablation site. It is necessary to provide an adequate seal around the thermocouple where the thermocouple is introduced into the ablation assembly.

It may also be desirable to include a mechanism to irrigate certain target areas with biocompatible fluids, such as saline solution. This irrigation may reduce or avoid excess or unwanted tissue damage, and blood coagulation and problems associated therewith. The ablation assembly may be provided with an external irrigation port or with an internal irrigation lumen.

In addition, it may desirable to monitor contact between the ablation assembly and the tissue at the target site to ensure treatment is rendered effectively. Such contact may be monitored using a force sensor provided within the ablation assembly. The force sensor may be an optical force sensor (e.g., a fiber optic force sensor). In at least some cases, fluid entering the force sensor may result in inaccurate force measurements. Sealing the force sensor in ablation catheters that also include thermocouples and irrigation conduits can present several challenges in catheter design. For example, increasing the size of the force sensor to accommodate a seal can increase strain on fiber optics thereof, leading to inaccurate force readings or excessive stress on the fiber optics.

Accordingly, a need exists for improved ablation catheter assemblies that include thermocouples and force sensors with suitable sealing mechanisms.

SUMMARY OF THE DISCLOSURE

The present disclosure is directed to an ablation catheter including an irrigation conduit having a proximal end and a distal end, and defining an irrigation lumen configured to carry irrigation fluid to a distal end of the ablation catheter. The ablation catheter also includes a force sensor that includes a deformable body coupled to the irrigation conduit adjacent the distal end thereof, and an electrode tip assembly coupled to the deformable body and extending distally therefrom. The electrode tip assembly defines an interior cavity in fluid communication with the irrigation lumen and an exterior cavity in which a distal portion of the deformable body is received. The ablation catheter further includes a seal disposed between the electrode tip assembly and the deformable body. The seal inhibits fluid flow between the interior cavity and the exterior cavity. The ablation catheter further includes a temperature sensor coupled to the electrode tip assembly and extending from the electrode tip assembly through the irrigation lumen.

The present disclosure is also directed to a method of assembling an ablation catheter, the method including routing a temperature sensor through an irrigation lumen defined by an irrigation conduit such that the temperature sensor extends out a of distal end of the irrigation conduit. The method also includes coupling a deformable body of a force sensor to the distal end of the irrigation conduit, positioning a seal adjacent a distal portion of the deformable body, and routing the temperature sensor into an electrode tip assembly that defines an interior cavity and an exterior cavity. The method also includes positioning the distal portion of the deformable body within the exterior cavity of the electrode tip assembly, and coupling the electrode tip assembly to the deformable body such that the electrode tip assembly extends distally from the deformable body and the interior cavity is in fluid communication with the irrigation lumen. The seal is disposed between the electrode tip assembly and the deformable body to inhibit fluid flow between the interior cavity and the exterior cavity. The method further includes coupling the temperature sensor to the electrode tip assembly such that the temperature sensor extends from the electrode tip assembly through the irrigation lumen.

The present disclosure is further direction to a catheter system including an ablation catheter and an ablation generator. The ablation catheter includes an irrigation conduit having a proximal end and a distal end, and defining an irrigation lumen configured to carry irrigation fluid to a distal end of the ablation catheter. The ablation catheter also includes a force sensor including a deformable body coupled to the irrigation conduit adjacent the distal end thereof, and an electrode tip assembly coupled to the deformable body and extending distally therefrom. The electrode tip assembly defines an interior cavity in fluid communication with the irrigation lumen and an exterior cavity in which a distal portion of the deformable body is received. The ablation catheter further includes a seal disposed between the electrode tip assembly and the deformable body. The seal inhibits fluid flow between the interior cavity and the exterior cavity. The ablation catheter further includes a temperature sensor coupled to the electrode tip assembly and extending from the electrode tip assembly through the irrigation lumen. The ablation generator is electrically coupled to the electrode tip assembly and configured to supply ablative energy thereto.

DETAILED DESCRIPTION OF THE DISCLOSURE

The present disclosure is directed to ablation systems and methods of forming the same and, more particularly, to ablation catheters including a force sensor and an electrode tip assembly sealed from the force sensor. Embodiments of the systems and methods disclosed herein facilitate providing an ablation catheter with a force sensor sealed form the electrode tip assembly and a temperature sensor, to therefore facilitate monitoring a temperature and an applied force during an ablation procedure. The temperature sensor is routed through an irrigation conduit, to reduce a likelihood of leaks adjacent to the force sensor that can adversely affect force measurements. This arrangement enables a simpler and more reliable seal between the force sensor and the electrode tip assembly, and also enables a reduced diameter force sensor, which reduces the likelihood of the force sensor being subjected to excessive stress or strain during operation. The ablation catheter described herein also includes a fluid manifold configured to accommodate the temperature sensor as well as improve the dispersion of irrigation fluid through the electrode tip assembly. The embodiments of the ablation catheter described herein facilitate faster assembly, a reduced number of components, reduced component cost, and reduced variability in assembly, which improves overall reliability of the ablation catheter.

Figure 1:
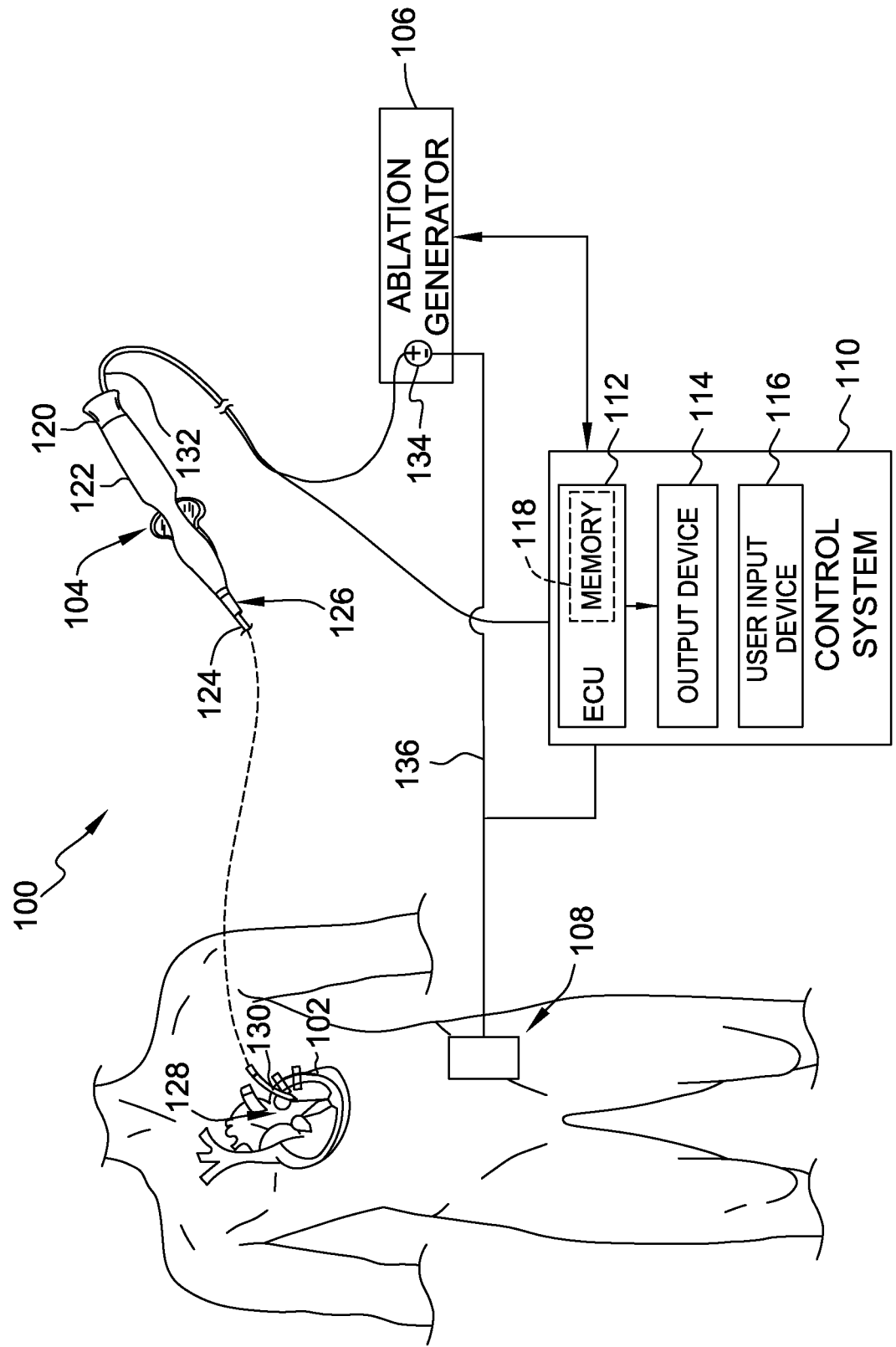
FIG. 1 is a schematic and block diagram view of an ablation system.

Referring now to the drawings, FIG. 1 illustrates one exemplary embodiment of an ablation system 100 for performing one or more diagnostic and/or therapeutic functions that include components for monitoring the temperature of an electrode before, during, and/or after an ablation procedure performed on tissue 102 of a patient, as well as monitoring the force of contact between the electrode and tissue 102 before, during, and/or after the ablation procedure. In the illustrative embodiment, tissue 102 is heart or cardiac tissue. It should be understood, however, that system 100 has equal applicability to ablation procedures on other tissues as well, and is not limited to ablation procedures on cardiac tissue.

System 100 includes a medical device (such as, for example, a catheter 104), an ablation generator 106, one or more return patch electrodes 108 (also referred to as dispersive or indifferent patch electrodes), and a control system 110 for communicating with and/or controlling one or more components of ablation system 100. Control system 110 may include, for example and without limitation, a controller or electronic control unit (ECU) 112, an output device 114, a user input device 116, and a memory 118. In some embodiments, control system 110 may be implemented in combination with, as part of, or incorporated within other systems and/or sub-systems of ablation system 100 including, for example and without limitation, ablation generator 106, imaging systems, mapping systems, navigation systems, and any other system or sub-system of ablation system 100.

Catheter 104 is provided for examination, diagnosis, and/or treatment of internal body tissues, such as cardiac tissue 102. In an exemplary embodiment, catheter 104 comprises a radio frequency (RF) ablation catheter. It should be understood, however, that catheter 104 is not limited to an RF ablation catheter. Rather, in other embodiments, catheter 104 may comprise an irrigated catheter and/or other types of ablation catheters (e.g., cryoablation, ultrasound, irreversible electroporation, balloon, basket, single electrode, bullet, etc.).

In an exemplary embodiment, catheter 104 is electrically connected to ablation generator 106 to allow for the delivery of RF energy. Catheter 104 may include a cable connector or interface 120, a handle 122, a shaft 124 having a proximal end 126 and distal end 128 (as used herein, "proximal" refers to a direction toward the end of catheter 104 near the operator, and "distal" refers to a direction away from the operator and (generally) inside the body of a subject or patient), and one or more electrodes 130 mounted in or on shaft 124 of catheter 104. In an exemplary embodiment, electrode 130 is disposed at or near distal end 128 of shaft 124, with electrode 130 comprising an ablation electrode disposed at the extreme distal end 128 of shaft 124 for contact with cardiac tissue 102. Catheter 104 further includes a thermocouple (not shown in FIG. 1) disposed within electrode 130 and a force sensor (also not shown in FIG. 1) disposed within and/or proximate to electrode 130. Catheter 104 may further include other components such as, for example and without limitation, sensors, additional electrodes (e.g., ring electrodes) and corresponding conductors or leads, thermocouples, or additional ablation elements, e.g., a high intensity focused ultrasound ablation element and the like.

Connector 120 provides mechanical and electrical connection(s) for cables 132 extending from ablation generator 106, control system 110, and other systems and/or sub-systems of ablation system 100. Connector 120 is disposed at the proximal end of catheter 104.

Handle 122 provides a location for the operator to hold catheter 104 and may further provide means for steering or guiding shaft 124 within the patient. For example, handle 122 may include means to change the length of a guidewire extending through catheter 104 to distal end 128 of shaft 124 to steer shaft 124. Handle 122 may have any suitable construction that enables the ablation system 100 to function as described herein. In another exemplary embodiment, catheter 104 may be robotically driven or controlled. Accordingly, rather than an operator manipulating a handle to steer or guide catheter 104, and shaft 124 thereof, in particular, a robot is used to manipulate catheter 104.

Shaft 124 is generally an elongated, tubular, flexible member configured for movement within the patient. Shaft 124 supports, for example and without limitation, electrode 130, the thermocouple, and force sensor associated therewith, associated conductors, and possibly additional electronics used for signal processing or conditioning. Shaft 124 also permits transport, delivery, and/or removal of fluids including irrigation fluids to the ablation site of tissue 102. Shaft 124 may additionally or alternatively permit transport, delivery, and/or removal of other fluids (cryogenic ablation fluids and/or bodily fluids), medicines, and/or surgical tools or instruments. Shaft 124 may be made from conventional materials such as polyurethane, and defines one or more lumens configured to house and/or transport at least electrical conductors, fluids, and/or surgical tools. Shaft 124 may be introduced into cardiac tissue 102 through a conventional introducer. Shaft 124 may then be steered or guided within cardiac tissue 102 to a desired location with guidewires or other means known in the art.

Ablation generator 106 generates, delivers, and controls RF energy output by ablation catheter 104 and electrode 130 thereof, in particular. In an exemplary embodiment, ablation generator 106 includes RF ablation signal source 134 configured to generate an ablation signal that is output across a pair of source connectors: a positive polarity connector SOURCE (+), which may be electrically connected to tip electrode 130 of catheter 104; and a negative polarity connector SOURCE (−), which may be electrically connected to the one or more return patch electrodes 108 (e.g., via a conductive lead or cable 136) disposed on the patient's skin.

It should be understood that the term connectors as used herein does not imply a particular type of physical interface mechanism, but is rather broadly contemplated to represent one or more electrical nodes. Source 134 is configured to generate a signal at a predetermined frequency in accordance with one or more user specified parameters (e.g., power, time, etc.) and under the control of various feedback sensing and control circuitry as is known in the art. Ablation system 100 may also monitor various parameters associated with the ablation procedure including, for example, impedance, the temperature at the distal tip of the catheter, applied ablation energy, and the position of the catheter, and provide feedback to the operator or another component within system 100 regarding these parameters.

Turning now to FIGS. 2-5, an exemplary ablation catheter 200 suitable for use with ablation system 100 is shown. Ablation catheter 200 may be substantially similar to catheter 104, and accordingly like features between catheter 104 and catheter 200 are labelled using like reference numerals. Specifically, ablation catheter 200 includes shaft 124 (FIG. 4) and electrode 130. In the exemplary embodiment, electrode 130 is embodied as a hollow elongate electrode tip assembly 202, which at least partially defines a distal end 204 of ablation catheter 200.

In the exemplary embodiment, electrode tip assembly 202 is a flexible electrode tip assembly, such as the electrode tip assembly described in U.S. Pat. No. 9,510,903, which is incorporated by reference herein in its entirety. For example, electrode tip assembly 202 includes a generally cylindrical sidewall 206 with irrigation fluid channels 208 extending therethrough. In some embodiments, fluid channels 208 are formed with an interlocking block pattern, but fluid channels 208 may have any suitable shape, orientation, and/or pattern that enables electrode tip assembly 202 to function as described herein. In the exemplary embodiment, fluid channels 208 are defined in cylindrical sidewall 206 and extend or perforate through the thickness of cylindrical sidewall 206 to improve flexibility of electrode tip assembly 202. The "flexibility" refers to flexing and bending along a longitudinal length of electrode tip assembly 202 relative to a longitudinal axis 210 (FIG. 4) thereof when electrode tip assembly 202 is placed under a load.

Electrode tip assembly 202 further includes a stem 212 disposed at a proximal end 214 thereof. Specifically, stem 212 extends proximally of cylindrical sidewall 206. Stem 212 includes a flange 216 and a cylindrical wall or collar 218 extending proximally from flange 216. Flange 216 extends proximally from and radially inward of cylindrical sidewall 206. In addition, electrode tip assembly 202 includes a cap 220 disposed at a distal end 222 thereof. Cap 220 is coupled to a distal end 224 of cylindrical sidewall 206.

In the exemplary embodiment, shaft 124 of ablation catheter 200 includes an irrigation conduit 226 extending therethrough. Alternatively, irrigation conduit 226 may extend alongside shaft 124 (e.g., as an external irrigation conduit). Irrigation conduit 226 has a proximal end 228 and a distal end 230 and defines an irrigation lumen 232 therethrough. Irrigation lumen 232 is configured to carry irrigation fluid (not shown) to distal end 204 of ablation catheter 200, specifically, to electrode tip assembly 202. In some embodiments, irrigation conduit 226 is formed from stainless steel. In other embodiments, irrigation conduit 226 is formed of any other suitable material.

Electrode tip assembly 202 is coupled to irrigation conduit 226 adjacent distal end 230 of irrigation conduit 226. Cylindrical sidewall 206 at least partially defines an interior cavity 234 of electrode tip assembly 202, where interior cavity 234 is in fluid communication with irrigation lumen 232. In particular, a distal end of irrigation lumen 232 (corresponding to distal end 230 of irrigation conduit 226) is positioned within interior cavity 234 such that irrigation fluid is dispensed from irrigation lumen 232 into interior cavity 234. Irrigation fluid is further dispensed through fluid channels 208 to tissue 102 (shown in FIG. 1). Cap 220 further defines interior cavity 234 and, more specifically, encloses interior cavity 234 at distal end 224 of cylindrical sidewall 206.

In the exemplary embodiment, stem 212 defines an exterior cavity 236 of electrode tip assembly 202. More particularly, cylindrical wall 218 of stem 212 defines exterior cavity 236. Exterior cavity 236 is proximal to interior cavity 234, and at least a portion of irrigation conduit 226 extends through exterior cavity 236 to interior cavity 234.

Electrode tip assembly 202 also includes a fluid manifold 240 disposed within interior cavity 234. In some embodiments, fluid manifold 240 is coupled to stem 212 of electrode tip assembly 202. For example, fluid manifold 240 may be adhered, welded, and/or otherwise mechanically coupled to flange 216 of stem 212. In the exemplary embodiment, fluid manifold 240 includes a tubular sidewall 242 extending distally from stem 212 and into interior cavity 234. Tubular sidewall 242 defines a plurality of fluid distribution holes 244 therein, where fluid distribution holes 244 are arranged circumferentially about tubular sidewall 242. Fluid manifold 240 is in fluid communication with distal end 230 of irrigation conduit 226 and is configured to disperse irrigation fluid therefrom into interior cavity 234. Specifically, fluid distribution holes 244 are arranged and oriented to disperse irrigation fluid radially outward from fluid manifold 240.

Figure 4:
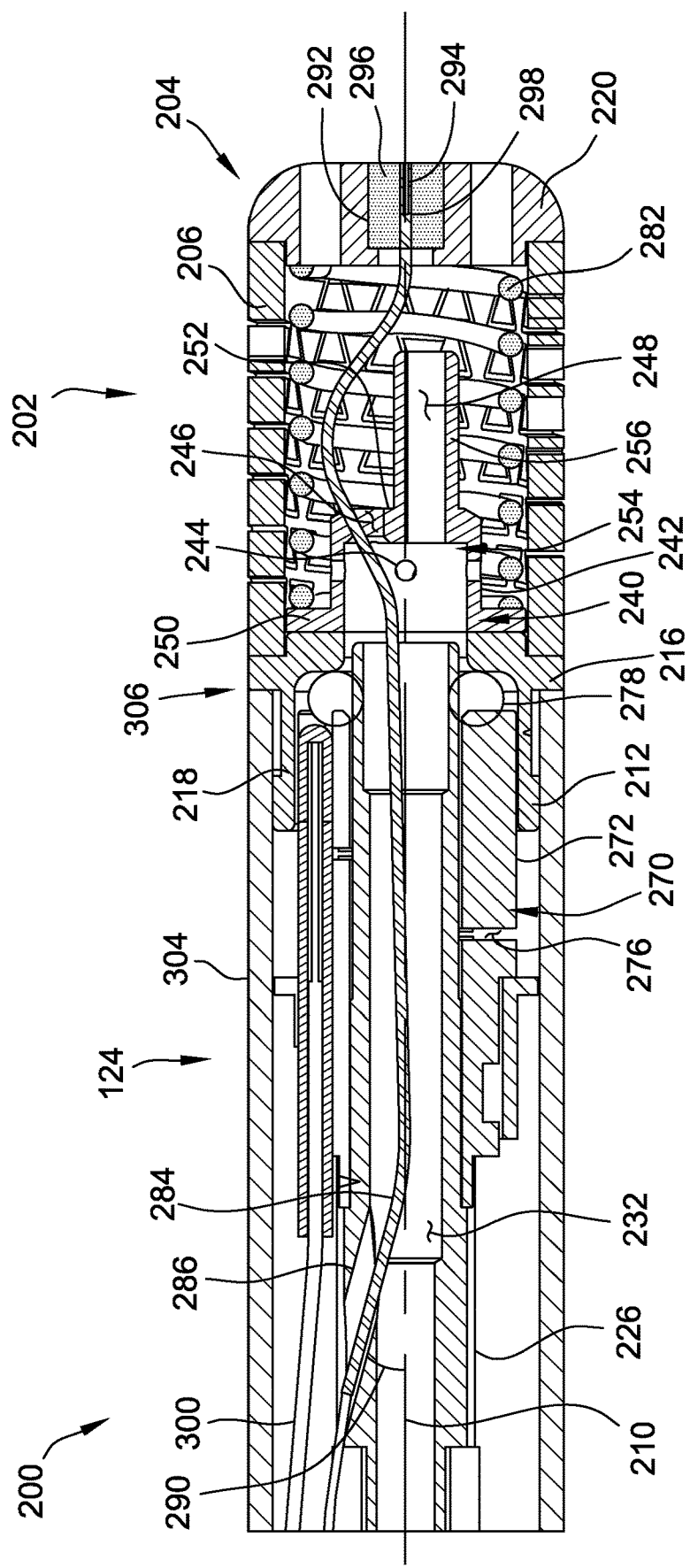
FIG. 4 is a sectional view of the ablation catheter shown in FIG. 2.

Moreover, in some embodiments, fluid manifold 240 defines a first axial fluid passage 246 and a second axial fluid passage 248. Axial fluid passages 246, 248 are configured to disperse irrigation fluid axially from fluid manifold 240. In one exemplary embodiment, as best seen in FIG. 4, axial fluid passages 246, 248 are each offset from a longitudinal centerline of fluid manifold 240, which corresponds to longitudinal axis 210 in the illustrated embodiment. In addition, in some embodiments, second axial fluid passage 248 has a greater length than first axial fluid passage 246. This arrangement of axial fluid passages 246, 248, in particular of second axial fluid passage 248, improves flow of irrigation fluid within interior cavity 234 (e.g., by moving the fluid flow from second axial fluid passage off-center).

Figure 5:
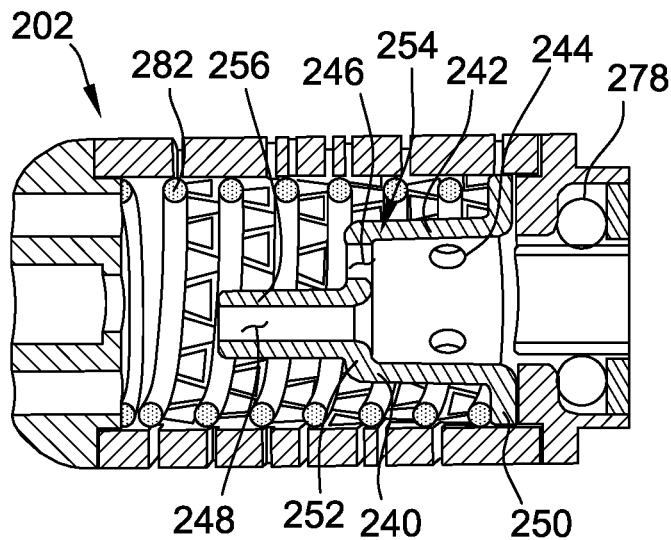
FIG. 5 is a sectional view of an electrode tip assembly of the ablation catheter shown in FIGS. 2-4.

In some embodiments, fluid manifold 240 is formed as a unitary piece, such as via a molding or machining process. In some such embodiments, as best shown in FIGS. 4 and 5, fluid manifold 240 includes an annular flange 250 positioned against and in engagement with stem 212 of electrode tip assembly 202 (e.g., against flange 216 of stem 212). Tubular sidewall 242 extends distally from annular flange 250. Fluid manifold 240 further includes a distal end cap 252 located at and extending radially inward from a distal end 254 of tubular sidewall 242, as well as a tubular extension 256 extending distally from distal end cap 252. In such embodiments, distal end cap 252 defines first axial fluid passage 246 therethrough, and tubular extension 256 defines second axial fluid passage 248. Distal end cap 252 may be substantially planar and oriented parallel to annular flange 250. Alternatively, distal end cap 252 may be obliquely angled with respect to tubular sidewall 242. In some embodiments, distal end cap 252 may further define addition fluid distribution holes 244 therein.

Figure 6:
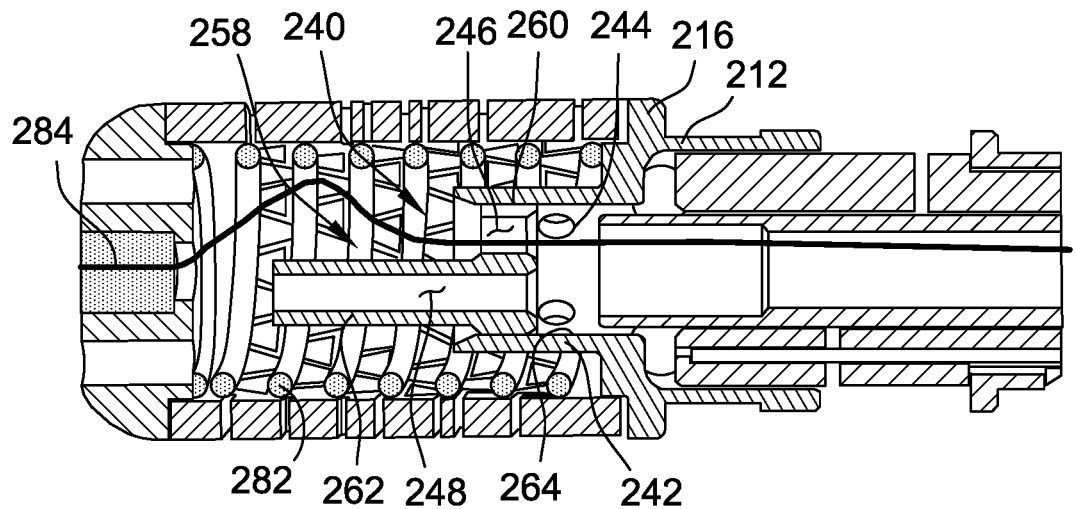
FIG. 6 is a sectional view of another alternative electrode tip assembly suitable for use with the ablation catheter shown in FIGS. 2-4.

In other embodiments, as shown in FIG. 6, fluid manifold 240 is at least partially formed as an extension of stem 212 of electrode tip assembly 202. Specifically, tubular side wall 242 is integral to and extends distally from flange 216 of stem 212. In such embodiments, fluid manifold 240 further includes an insert 258 received within tubular sidewall 242. Insert 258 includes a base 260 and a tubular extension 262 extending distally from base 260. In such embodiments, base 260 defines first axial fluid passage 246, and tubular extension 262 defines second axial fluid passage 248. Base 260 is sized and shaped to engage with an inner surface 264 of tubular sidewall 242. Base 260 may be retained against inner surface 264 of tubular sidewall 242 via a friction fit and/or via adhesive, welding, and/or any other suitable coupling method.

In alternative embodiments, fluid manifold 240 is formed form two or more pieces that are subsequently coupled together to form fluid manifold 240. For example, fluid manifold 240 may be formed form a base that many include a flange, a tubular side wall, and a distal end cap, and from a separate tubular extension that is configured to be coupled to the base.

Ablation catheter 200 further includes a force sensor 270 coupled to irrigation conduit 226 adjacent distal end 230. In the exemplary embodiment, force sensor 270 includes a generally tubular deformable body 272 that extends circumferentially about irrigation conduit 226 adjacent distal end 230 of irrigation conduit 226. Electrode tip assembly 202 is further coupled to force sensor 270. In particular, electrode tip assembly 202 is coupled to deformable body 272 of force sensor 270 and extends distally therefrom to at least partially define distal end 204 of ablation catheter 200. In the exemplary embodiment, exterior cavity 236 receives at least a portion of deformable body 272 therein. For example, exterior cavity 236 receives a distal portion 274 of deformable body 272 therein.

Force sensor 270 may include any suitable force sensor, including those described in U.S. Pat. Nos. 8,435,232 and 9,597,036, each of which is incorporated by reference herein in its entirety. For example, force sensor 270 is an optical fiber sensor that senses longitudinal and/or lateral forces applied to ablation catheter 200 by optically sensing deformation of deformable body 272. In particular, a plurality of air gaps 276 are defined in deformable body 272 that enable the optical sensing of the deformation of deformable body 272.

In the exemplary embodiment, a seal 278 is positioned within exterior cavity 236 distally of distal portion 274 of deformable body 272. Seal 278 is disposed between electrode tip assembly 202 and deformable body 272 to inhibit fluid flow (e.g., of irrigation fluid) between interior cavity 234 and exterior cavity 236. Specifically, seal 278 is engaged with flange 216 of stem 212 (e.g., with a proximally-facing surface 280 of flange 216) and distal portion 274 of deformable body 272 to provide a seal between interior cavity 234 and exterior cavity 236. In some embodiments, seal 278 includes a flexible or elastomeric annular component (e.g., a silicone O-ring). In other embodiments, seal 278 includes any other suitable sealing component.

Electrode tip assembly 202 further includes a spring 282 positioned within interior cavity 234 against cylindrical sidewall 206. Spring 282 is configured to provide a desired level of rigidity to electrode tip assembly 202, and to improve force measurements taken by force sensor 270. In some embodiments, as shown in FIGS. 2-5, spring 282 is engaged against annular flange 250 of fluid manifold 240 to bias fluid manifold 240 against flange 216 of stem 212.

Ablation catheter 200 further includes a temperature sensor 284. Temperature sensor 284 extends distally through at least a portion of irrigation conduit 226 and into electrode tip assembly 202. Specifically, irrigation conduit 226 defines a through hole 286 therein to receive temperature sensor 284 and associated wiring 288 therethrough. Through hole 286 is oriented at an oblique angle 290 with respect to longitudinal axis 210. Temperature sensor 284 extends through hole 286 and into irrigation conduit 226 (i.e., into irrigation lumen 232). In some embodiments, through hole 286 forms an angle 290 of about 15° with respect to longitudinal axis 210, such that temperature sensor 284 may be easily routed through through hole 286 and longitudinally through irrigation lumen 232. Angle 290 may be, for example, between about 10° and about 20° to facilitate assembly of ablation catheter 200 as described herein. Temperature sensor 284 extends through distal end 230 of irrigation conduit 226 and into fluid manifold 240, through which temperature sensor 284 extends into electrode tip assembly 202 (e.g., through interior cavity 234).

If temperature sensor 284 were routed into electrode tip assembly 202 at a more distal location and/or not through irrigation conduit 226 (e.g., through stem 212), as is contemplated in at least some alternative or prior catheters, such an arrangement presents difficulties with respect to adequately sealing force sensor 270 from interior cavity. Specifically, if air gaps 276 are exposed to fluids (e.g., water, irrigation fluids, bodily fluids, etc.), the optical components of force sensor 270 may be unable to accurately detect deformation of deformable body 272, and, therefore, force measurements may be inaccurate. In one proposed solution, an adhesive or epoxy material may be applied to an interface between the force sensor and the tip assembly to inhibit ingress of irrigation fluid to the force sensor. However, such a seal is manually applied and, if not properly applied, could provide an additional source of interference with the force sensor that could lead to inaccurate force measurements.

Accordingly, ablation catheter 200 provides an improvement over such catheter designs by routing temperature sensor 284 through irrigation conduit 226 at a location proximal to deformable body 272 and into interior cavity 234 at a location distal of deformable body. Therefore, ablation catheter 200 includes seal 278 that is positioned between electrode tip assembly 202 and deformable body 272 during assembly of ablation catheter 200 to seal interior cavity 234 from deformable body 272. Seal 278 is not prone to misapplication or improper positioning, and as such is less susceptible to fluid leaks that could interfere with force measurements taken by force sensor 270.

Temperature sensor 284 is coupled to electrode tip assembly 202 at distal end 222 thereof. More specifically, temperature sensor 284 is coupled to cap 220 of electrode tip assembly 202. Cap 220 defines a counterbore 292 extending axially therethrough, and a distal end 294 of temperature sensor 284 is anchored or potted within counterbore 292 via an adhesive or epoxy material 296. In some embodiments, temperature sensor 284 includes a thermocouple sensor 298 at distal end 294 thereof.

In the exemplary embodiment, temperature sensor 284 extends from fluid manifold 240 and into interior cavity 234 through first axial fluid passage 246. By routing temperature sensor 284 through first axial fluid passage 246 (and, therefore, not through second axial fluid passage 248), sufficient fluid flow through second axial fluid passage 248 can be ensured. That is, temperature sensor 284 does not interfere with fluid flow through second axial fluid passage 248.

Moreover, temperature sensor 284 extends through electrode tip assembly 202 in a non-linear orientation (e.g., in a curved or partially helical configuration). Accordingly, temperature sensor 284 is less prone to load-sharing with force sensor 270, which could lead to inaccurate force measurements, as compared to at least some conventional catheters with temperature sensors that extend linearly through an electrode tip (e.g., parallel to and/or co-axial with a longitudinal axis thereof).

In some embodiments, temperature sensor 284 includes an external coating (not shown) disposed thereon. The external coating may be formed from a material that forms a heat shrink coating on the temperature sensors. Suitable materials include, for example and without limitation, polymeric materials such as polyethylene terephthalate (PET), polyether ether ketone (PEEK), and the like. The external coating may insulate and/or otherwise protect temperature sensor 284 (including wiring 288) from the irrigation fluid in irrigation conduit 226 and/or interior cavity 234.

Figure 2:
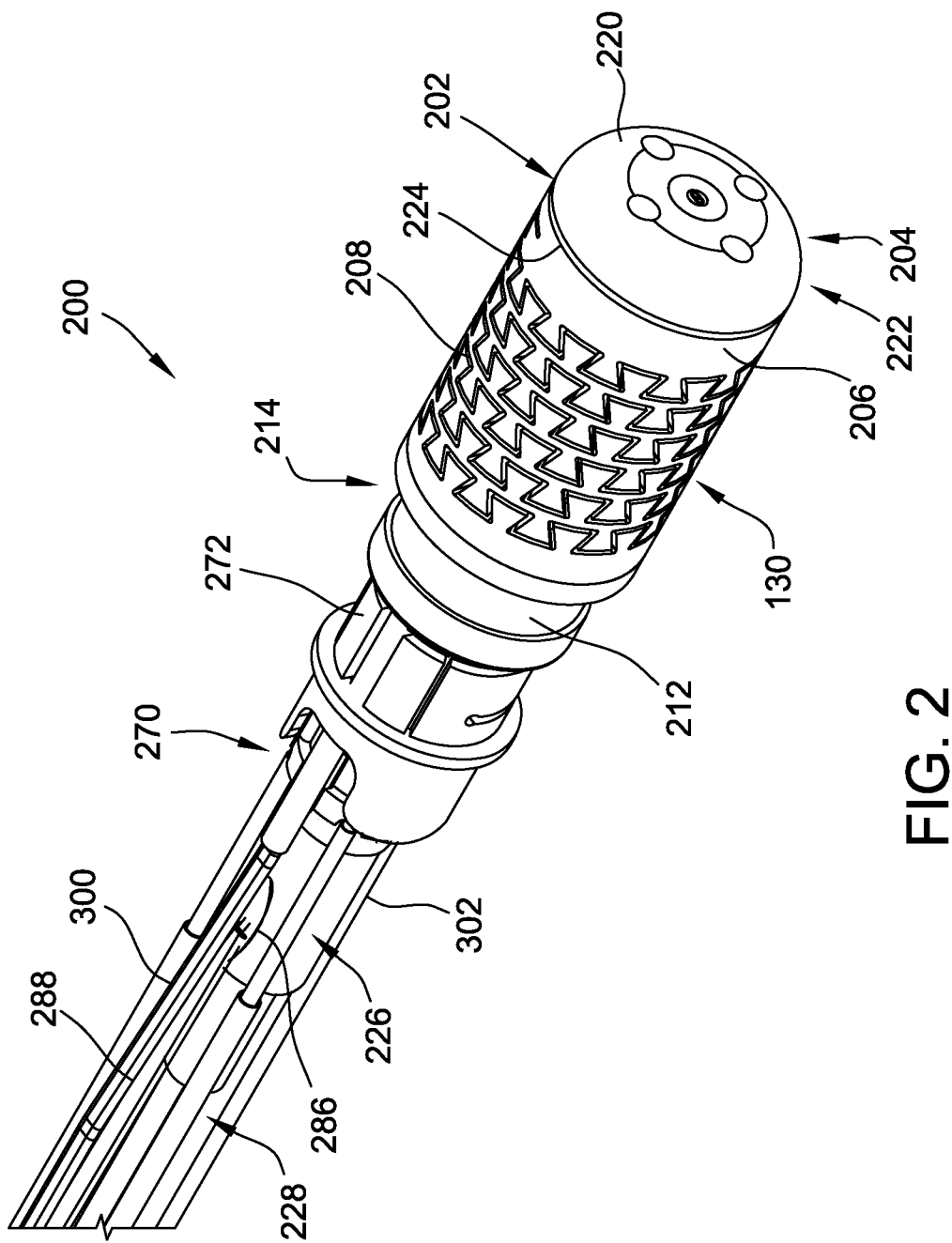
FIG. 2 is a perspective view of one exemplary embodiment of an ablation catheter suitable for use with the ablation system of FIG. 1.
Figure 3:
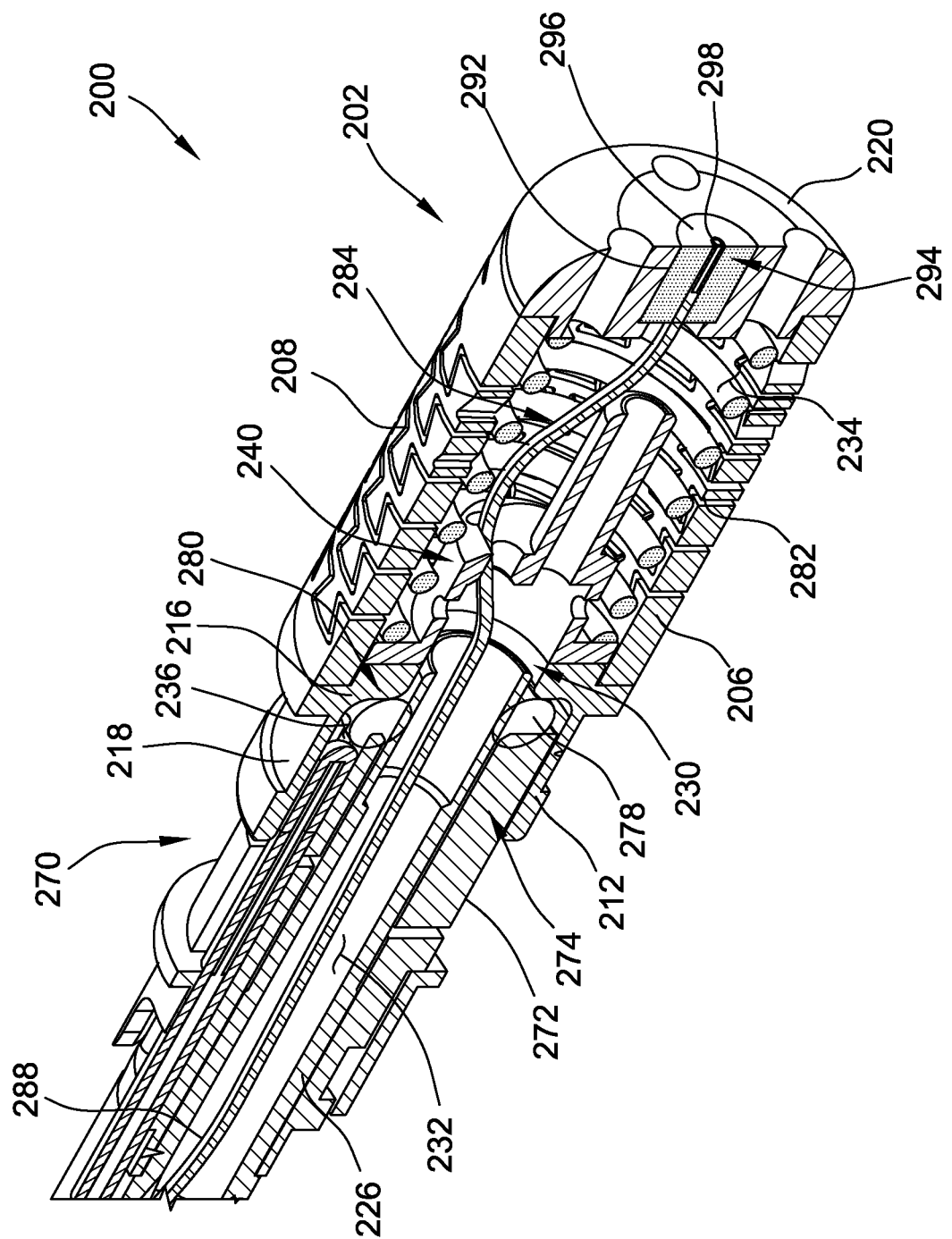
FIG. 3 is a cutaway view of the ablation catheter shown in FIG. 2.

In the embodiment of FIGS. 2-4, irrigation conduit 226, deformable body 272, and electrode tip assembly 202 (including fluid manifold 240) are generally coaxial and share longitudinal axis 210. In alternative embodiments, one or more of these components may be other than co-axial with any other component. In addition, temperature sensor 284 is coupled to cap 220 where longitudinal axis 210 intersects cap 220, or at a center of cap 220 and/or a longitudinal center of electrode tip assembly 202. Such placement of temperature sensor 284 may improve the usability of the temperature measurements, as off-center temperature measurements may not be fully indicative of the state of tissue 102 at the ablation site. In other embodiments, temperature sensor 284 may be otherwise positioned.

Ablation catheter 200 may include additional and/or alternative components. In the embodiment of FIGS. 2-4, ablation catheter 200 includes wiring 300 configured to transmit power from ablation generator 106 (shown in FIG. 1) to electrode tip assembly 202. For example, wiring 300 is electrically coupled (e.g., welded) to electrode tip assembly 202 (e.g., via stem 212). Ablation catheter 200 may further include an additional temperature sensor 302 to measure a temperature of and/or adjacent to force sensor 270. These temperature measurements can be used to account for any effect of heat on force measurements form force sensor 270.

In the exemplary embodiment, shaft 124 includes a tube 304 configured to house various components of ablation catheter 200. Tube 304 extends from proximal end 126 of shaft 124 to electrode tip assembly 202. For example, a distal end 306 of tube 304 abuts flange 216 of stem 212. Tube 304 prevents fluid intrusion to the housed components of ablation catheter 200, such as force sensor 270, wiring 300, temperature sensor(s) 284, 302, and the like.

Figure 7:
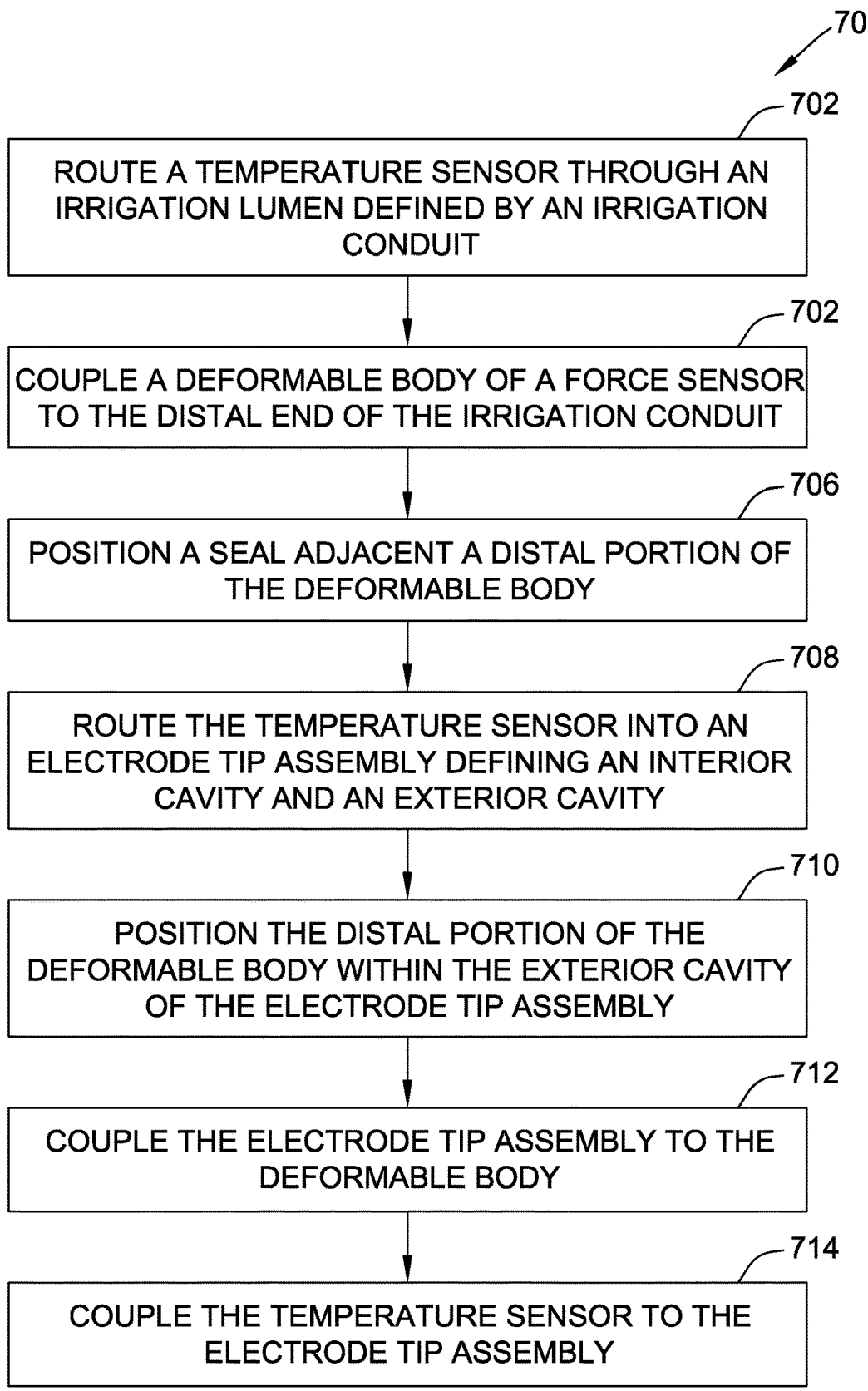
FIG. 7 is a flow diagram illustrating one embodiment of a method of assembling an ablation catheter.

FIG. 7 is a flow diagram illustrating one embodiment of a method 700 of assembling an ablation catheter, such as ablation catheter 200 (shown in FIGS. 2-6). In some cases, method 700 is performed manually (e.g., by a human operator).

In the exemplary embodiment, method 700 includes routing 702 a temperature sensor (e.g., temperature sensor 284) through an irrigation lumen (e.g., irrigation lumen 232) defined by an irrigation conduit (e.g., irrigation conduit 226) such that the temperature sensor extends out of distal end of the irrigation conduit. In some embodiments, routing 702 includes routing the temperature sensor through a through hole (e.g., through hole 286) formed in the irrigation conduit and oriented at an oblique angle with respect to a longitudinal axis of the irrigation conduit.

Method 700 also includes coupling 704 a deformable body (e.g., deformable body 272) of a force sensor (e.g., force sensor 270) to the distal end of the irrigation conduit, and positioning 706 a seal (e.g., seal 278) adjacent a distal portion of the deformable body. In some embodiments, positioning 706 includes positioning an elastomeric O-ring against a distal end of the deformable body.

Method 700 further includes routing 708 the temperature sensor into an electrode tip assembly (e.g., electrode tip assembly 202). As described herein, the electrode tip assembly defines an interior cavity and an exterior cavity. In some embodiments, the electrode tip assembly further includes a fluid manifold (e.g., fluid manifold 240) disposed within the interior cavity and configured to disperse irrigation fluid from the irrigation conduit. The fluid manifold defines first and second axial fluid passages configured to disperse irrigation fluid axially from the fluid manifold. The first and second axial fluid passages are offset from a longitudinal centerline of the fluid manifold. In such embodiments, routing 708 may include routing the temperature sensor through one of the first and second axial fluid passages.

Method 700 also includes positioning 710 the distal portion of the deformable body within the exterior cavity of the electrode tip assembly. Positioning 710 may further include positioning the seal within the exterior cavity, between the distal portion of the deformable body and a proximal portion of the electrode tip assembly (e.g., against flange 216 of stem 212).

Method 700 further includes coupling 712 the electrode tip assembly to the deformable body such that the electrode tip assembly extends distally from the deformable body and the interior cavity is in fluid communication with the irrigation lumen. As a result of coupling 712, the seal is disposed between the electrode tip assembly and the deformable body to inhibit fluid flow between the interior cavity and the exterior cavity. In some embodiments, coupling 712 includes compressing the seal between the electrode tip assembly and the deformable body.

Method 700 further includes coupling 714 the temperature sensor to the electrode tip assembly such that the temperature sensor extends from the electrode tip assembly through the irrigation lumen. Coupling 714 may include potting or otherwise fixing the temperature sensor in a distal cap (e.g., distal cap 220) of the electrode tip assembly.

In some embodiments, the electrode tip assembly also includes a stem (e.g., stem 212) disposed at a proximal end of the electrode tip assembly and defining the exterior cavity, a cylindrical sidewall (e.g., cylindrical sidewall 206) extending distally from the stem and defining the interior cavity, and a cap coupled to the cylindrical sidewall at a distal end thereof and enclosing the interior cavity. In such embodiments, coupling 714 may include potting a distal end of the temperature sensor within a counterbore defined in the cap.

Although certain steps of the example method are numbered, such numbering does not indicate that the steps must be performed in the order listed. Thus, particular steps need not be performed in the exact order they are presented, unless the description thereof specifically require such order. The steps may be performed in the order listed, or in another suitable order.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the invention, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ablation catheter comprising:
    an irrigation conduit having a proximal end and a distal end, the irrigation conduit defining an irrigation lumen configured to carry irrigation fluid to a distal end of the ablation catheter;
    a force sensor comprising a deformable body coupled to the irrigation conduit adjacent the distal end thereof;
    an electrode tip assembly coupled to the deformable body and extending distally therefrom, wherein the electrode tip assembly defines an interior cavity in fluid communication with the irrigation lumen and an exterior cavity in which a distal portion of the deformable body is received, the distal portion of the deformable body terminating at a distal end;
    a seal disposed between the electrode tip assembly and the distal end of the deformable body, wherein the seal engages the electrode tip assembly and the distal end of the deformable body to inhibit fluid flow between the interior cavity and the exterior cavity; and
    a temperature sensor coupled to the electrode tip assembly and extending from the electrode tip assembly through the irrigation lumen.

2. The ablation catheter of claim 1, wherein the electrode tip assembly comprises:
    a stem disposed at a proximal end of the electrode tip assembly and defining the exterior cavity; and
    a cylindrical sidewall extending distally from the stem and defining the interior cavity.

3. The ablation catheter of claim 2, wherein the stem comprises a flange and a cylindrical wall extending proximally from the flange, wherein the cylindrical wall defines the exterior cavity in which the deformable body distal portion is received, and wherein the seal is disposed between and in engagement with the flange and the deformable body distal portion.

4. The ablation catheter of claim 2, wherein the electrode tip assembly further comprises a cap coupled to the cylindrical sidewall at a distal end thereof and enclosing the interior cavity, wherein the cap defines a counterbore extending axially through the cap, and wherein a distal end of the temperature sensor is potted within the counterbore.

5. The ablation catheter of claim 2, wherein the electrode tip assembly further comprises a fluid manifold disposed within the interior cavity and configured to disperse irrigation fluid from the irrigation conduit, wherein the fluid manifold comprises a tubular sidewall extending distally from the stem, the tubular sidewall defining a plurality of fluid distribution holes therein, wherein said fluid distribution holes are oriented to disperse irrigation fluid radially outward from the fluid manifold.

6. The ablation catheter of claim 5, wherein the fluid manifold defines first and second axial fluid passages configured to disperse irrigation fluid axially from the fluid manifold, wherein the first and second axial fluid passages are offset from a longitudinal centerline of the fluid manifold, and wherein the second axial fluid passage has a greater length than the first axial fluid passage.

7. The ablation catheter of claim 6, wherein the temperature sensor extends through the first axial fluid passage.

8. The ablation catheter of claim 6, wherein the fluid manifold further comprises an insert received within the tubular sidewall, wherein the insert comprises a base and a tubular extension extending distally from the base, wherein the base defines the first axial fluid passage and wherein the tubular extension defines the second axial fluid passage.

9. The ablation catheter of claim 6, wherein the fluid manifold is formed as a unitary piece, and wherein the fluid manifold further comprises:
    an annular flange disposed in engagement with the stem, wherein the tubular sidewall extends distally from the annular flange;
    a distal end cap located at a distal end of the tubular sidewall, wherein the distal end cap defines the first axial fluid passage; and
    a tubular extension extending distally from the distal end cap, wherein the tubular extension defines the second axial fluid passage.

10. The ablation catheter of claim 9, wherein the electrode tip assembly further comprises a spring disposed in engagement with the annular flange to bias the fluid manifold against the stem.

11. The ablation catheter of claim 2, wherein the cylindrical sidewall includes at least one irrigation fluid channel defined therein and extending therethrough, wherein the at least one irrigation fluid channel provides flexibility in the sidewall for bending movement of the electrode tip assembly relative to a longitudinal axis of the sidewall when the electrode tip assembly is placed under a load.

12. The ablation catheter of claim 1, wherein the electrode tip assembly is a flexible electrode tip assembly.

13. The ablation catheter of claim 1, wherein the irrigation conduit defines a through hole oriented at an oblique angle with respect to a longitudinal axis of the irrigation conduit, and wherein the temperature sensor extends through the through hole.

14. The ablation catheter of claim 1, wherein the seal comprises an elastomeric O-ring.

15. The ablation catheter of claim 1, wherein the temperature sensor comprises a thermocouple.

16. A method of assembling an ablation catheter, said method comprising:
   routing a temperature sensor through an irrigation lumen defined by an irrigation conduit such that the temperature sensor extends out of a distal end of the irrigation conduit;
   coupling a deformable body of a force sensor to the distal end of the irrigation conduit the deformable body including a distal portion that terminates at a distal end of the deformable body;
   positioning a seal adjacent the distal end of the deformable body;
   routing the temperature sensor into an electrode tip assembly, wherein the electrode tip assembly defines an interior cavity and an exterior cavity;
   positioning the distal portion of the deformable body within the exterior cavity of the electrode tip assembly;
   coupling the electrode tip assembly to the deformable body such that the electrode tip assembly extends distally from the deformable body and the interior cavity is in fluid communication with the irrigation lumen, wherein the seal is disposed between the electrode tip assembly and the distal end of the deformable body and engages the electrode tip assembly and the distal end of the deformable body to inhibit fluid flow between the interior cavity and the exterior cavity; and
   coupling the temperature sensor to the electrode tip assembly such that the temperature sensor extends from the electrode tip assembly through the irrigation lumen.

17. The method of claim 16, wherein the electrode tip assembly comprises:
   a stem disposed at a proximal end of the electrode tip assembly and defining the exterior cavity;
   a cylindrical sidewall extending distally from the stem and defining the interior cavity; and
   a cap coupled to the cylindrical sidewall at a distal end thereof and enclosing the interior cavity,
   wherein coupling the temperature sensor to the electrode tip assembly comprises potting a distal end of the temperature sensor within a counterbore defined in the cap.

18. The method of claim 16, wherein the electrode tip assembly further comprises a fluid manifold disposed within the interior cavity and configured to disperse irrigation fluid from the irrigation conduit, wherein the fluid manifold defines first and second axial fluid passages configured to disperse irrigation fluid axially from the fluid manifold, wherein the first and second axial fluid passages are offset from a longitudinal centerline of the fluid manifold, wherein routing the temperature sensor into an electrode tip assembly comprises routing the temperature sensor through one of the first and second axial fluid passages.

19. The method of claim 16, wherein routing a temperature sensor through an irrigation lumen comprises routing the temperature sensor through a through hole formed in the irrigation conduit and oriented at an oblique angle with respect to a longitudinal axis of the irrigation conduit.

20. A catheter system comprising:
   an ablation catheter comprising:
      an irrigation conduit having a proximal end and a distal end, the irrigation conduit defining an irrigation lumen configured to carry irrigation fluid to a distal end of the ablation catheter;
      a force sensor comprising a deformable body coupled to the irrigation conduit adjacent the distal end thereof;
      an electrode tip assembly coupled to the deformable body and extending distally therefrom, wherein the electrode tip assembly defines an interior cavity in fluid communication with the irrigation lumen and an exterior cavity in which a distal portion of the deformable body is received, the distal portion of the deformable body terminating at a distal end;
      a seal disposed between the electrode tip assembly and the distal end of the deformable body, wherein the seal engages the electrode tip assembly and the distal end of the deformable body to inhibit fluid flow between the interior cavity and the exterior cavity; and
      a temperature sensor coupled to the electrode tip assembly and extending from the electrode tip assembly through the irrigation lumen; and
   an ablation generator electrically coupled to the electrode tip assembly and configured to supply ablative energy thereto.

* * * * *